(12) United States Patent
Martin et al.

(10) Patent No.: US 8,021,402 B2
(45) Date of Patent: Sep. 20, 2011

(54) DISTAL RADIUS PLATE

(75) Inventors: Amanda Martin, Norton, OH (US);
David B. Kay, Akron, OH (US); Lee A. Strnad, Broadview Hts., OH (US); G. Martin Wynkoop, Gainesville, FL (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1192 days.

(21) Appl. No.: 11/713,856

(22) Filed: Mar. 5, 2007

(65) Prior Publication Data
US 2007/0265629 A1   Nov. 15, 2007

Related U.S. Application Data

(60) Provisional application No. 60/779,865, filed on Mar. 7, 2006.

(51) Int. Cl.
*A61B 17/80* (2006.01)
(52) U.S. Cl. .......................................... 606/286; 606/291
(58) Field of Classification Search .......... 606/280–297, 606/70–71
See application file for complete search history.

(56) References Cited

U.S. PATENT DOCUMENTS

| | | | | |
|---|---|---|---|---|
| 3,741,205 A | * | 6/1973 | Markolf et al. | 606/291 |
| 4,388,921 A | * | 6/1983 | Sutter et al. | 606/71 |
| 4,573,458 A | * | 3/1986 | Lower | 606/280 |
| 4,988,350 A | * | 1/1991 | Herzberg | 606/65 |
| 5,015,248 A | * | 5/1991 | Burstein et al. | 606/74 |
| 5,197,966 A | | 3/1993 | Sommerkamp | |
| 5,531,746 A | * | 7/1996 | Errico et al. | 606/287 |
| 5,586,985 A | * | 12/1996 | Putnam et al. | 606/86 B |
| 5,607,426 A | * | 3/1997 | Ralph et al. | 606/287 |
| 5,728,099 A | * | 3/1998 | Tellman et al. | 606/65 |
| 5,749,872 A | * | 5/1998 | Kyle et al. | 606/66 |
| 5,876,402 A | * | 3/1999 | Errico et al. | 606/287 |
| 5,973,223 A | * | 10/1999 | Tellman et al. | 606/65 |
| 6,096,040 A | * | 8/2000 | Esser | 606/280 |
| 6,221,073 B1 | * | 4/2001 | Weiss et al. | 606/60 |
| D443,060 S | * | 5/2001 | Benirschke et al. | D24/155 |
| 6,235,032 B1 | * | 5/2001 | Link | 606/280 |

(Continued)

OTHER PUBLICATIONS

New Trauma Products from AO Development, Jun. 2006 (p. 9).

*Primary Examiner* — Eduardo C Robert
*Assistant Examiner* — Mary Hoffman
(74) *Attorney, Agent, or Firm* — Hudak, Shunk & Farine Co. LPA

(57) ABSTRACT

A distal radius plate having a head with a complex palm shaped profile which flares from the sides of the plate to a leading edge that includes a central oblique linking area that helps to mark the placement of the plate relative to the radius. Further, the plate includes an oblique depression that extends from the rounded pinky side of the head and gradually morphs into the elevated styloid prominence in one diagonal direction, and rises less gradually upward into the lunate prominence on the other side of the head. A proximal plate portion mimics the spiral of the radial bone as it spirals along the longitudinal axis, and includes a tighter radial bend. The head includes holes or bores for pegs which extend into the distal portion of the radius to lock fragments into position. In the first embodiment, the angles of the pegs are fixed. In a second embodiment, one or more of the peg holes are provided with a variable axis locking mechanism assembly and the remaining holes are fixed.

23 Claims, 13 Drawing Sheets

U.S. PATENT DOCUMENTS

| | | | |
|---|---|---|---|
| 6,358,250 B1 | 3/2002 | Orbay | |
| 6,364,882 B1 | 4/2002 | Orbay | |
| 6,488,685 B1 * | 12/2002 | Manderson | 606/60 |
| 6,508,819 B1 | 1/2003 | Orbay | |
| 6,623,486 B1 | 9/2003 | Weaver et al. | |
| 6,652,530 B2 * | 11/2003 | Ip et al. | 606/284 |
| 6,712,820 B2 | 3/2004 | Orbay | |
| 7,335,204 B2 * | 2/2008 | Tornier | 606/284 |
| D576,731 S * | 9/2008 | Strnad et al. | D24/155 |
| D589,148 S * | 3/2009 | Strnad et al. | D24/155 |
| 2002/0013587 A1 * | 1/2002 | Winquist et al. | 606/69 |
| 2002/0156474 A1 * | 10/2002 | Wack et al. | 606/69 |
| 2003/0105461 A1 * | 6/2003 | Putnam | 606/69 |
| 2003/0114856 A1 * | 6/2003 | Nathanson et al. | 606/70 |
| 2004/0059334 A1 | 3/2004 | Weaver et al. | |
| 2004/0102778 A1 * | 5/2004 | Huebner et al. | 606/71 |
| 2004/0153073 A1 | 8/2004 | Orbay | |
| 2004/0167522 A1 * | 8/2004 | Niederberger et al. | 606/69 |
| 2004/0193155 A1 | 9/2004 | Castaneda | |
| 2005/0010226 A1 * | 1/2005 | Grady et al. | 606/69 |
| 2005/0049594 A1 * | 3/2005 | Wack et al. | 606/69 |
| 2005/0065522 A1 | 3/2005 | Orbay | |
| 2005/0080421 A1 | 4/2005 | Weaver et al. | |
| 2005/0085818 A1 | 4/2005 | Huebner | |
| 2005/0240187 A1 * | 10/2005 | Huebner et al. | 606/69 |
| 2005/0245931 A1 | 11/2005 | Orbay | |
| 2006/0173458 A1 * | 8/2006 | Forstein et al. | 606/69 |
| 2006/0241608 A1 * | 10/2006 | Myerson et al. | 606/69 |
| 2006/0259039 A1 | 11/2006 | Pitkanen et al. | |
| 2007/0088360 A1 * | 4/2007 | Orbay et al. | 606/69 |
| 2007/0233106 A1 * | 10/2007 | Horan et al. | 606/69 |
| 2008/0275510 A1 * | 11/2008 | Schonhardt et al. | 606/286 |
| 2010/0125300 A1 * | 5/2010 | Blitz et al. | 606/281 |
| 2010/0152783 A1 * | 6/2010 | Borostyankoi et al. | 606/281 |
| 2010/0305618 A1 * | 12/2010 | Kay et al. | 606/280 |

* cited by examiner

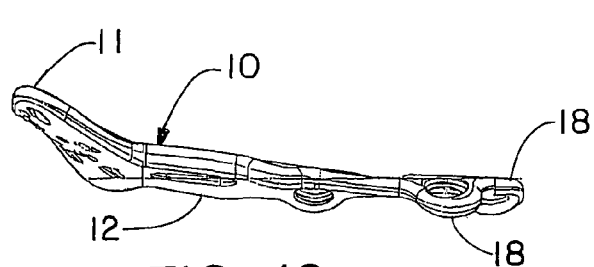
FIG.-12
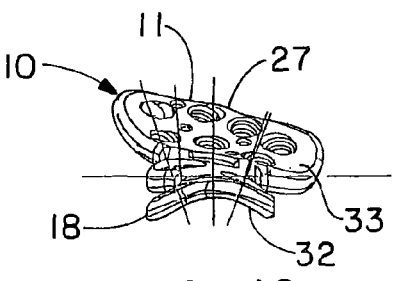
FIG.-13
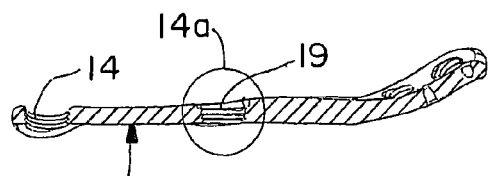
FIG.-14
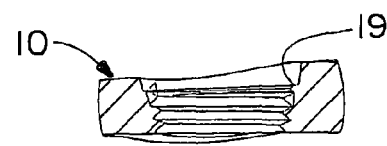
FIG.-14A
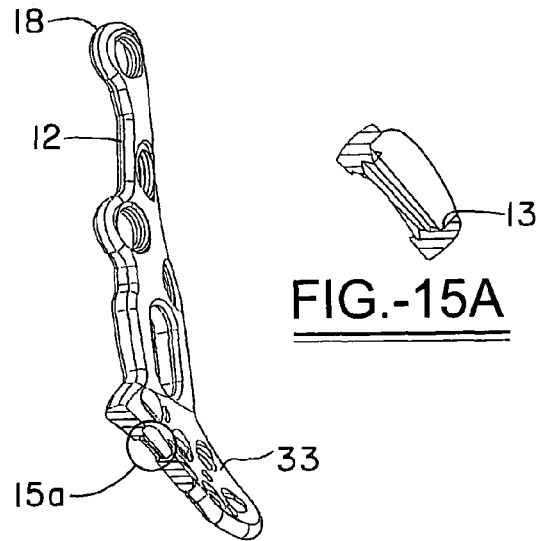
FIG.-15A
FIG.-15
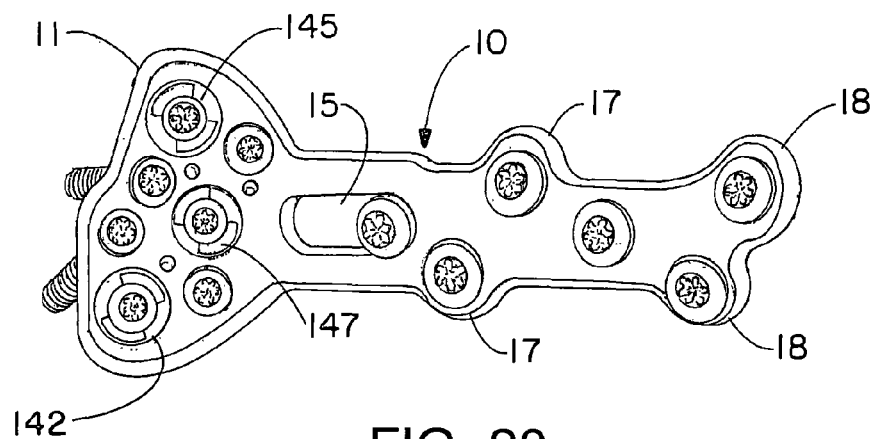
FIG.-20

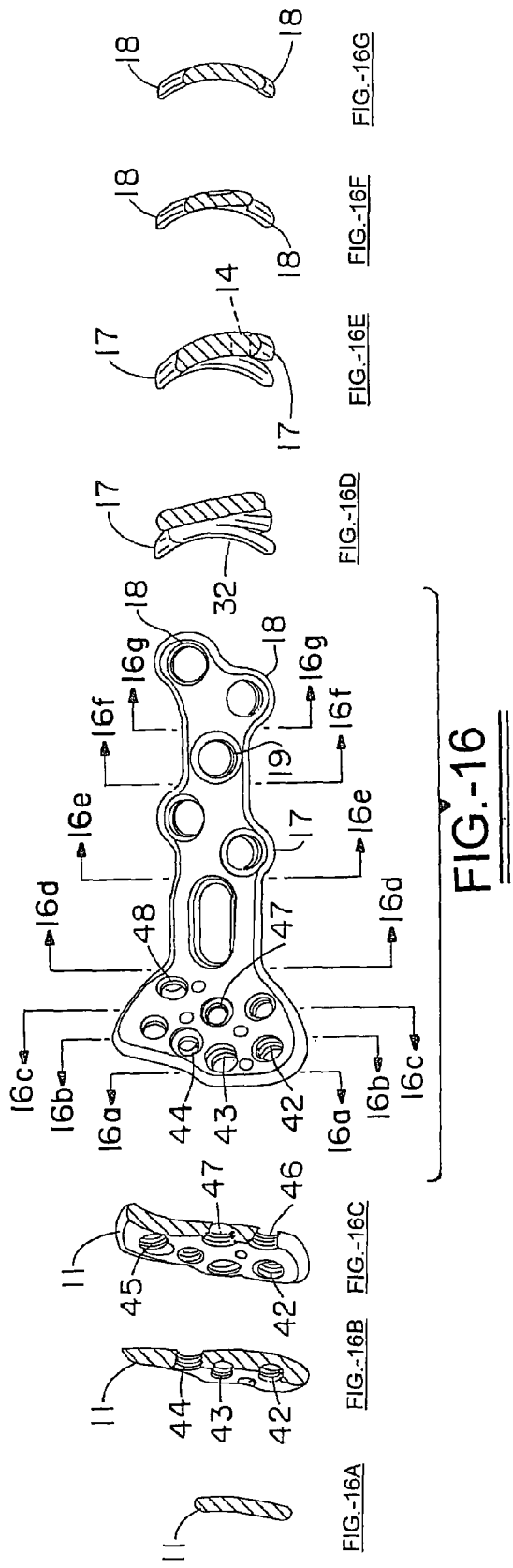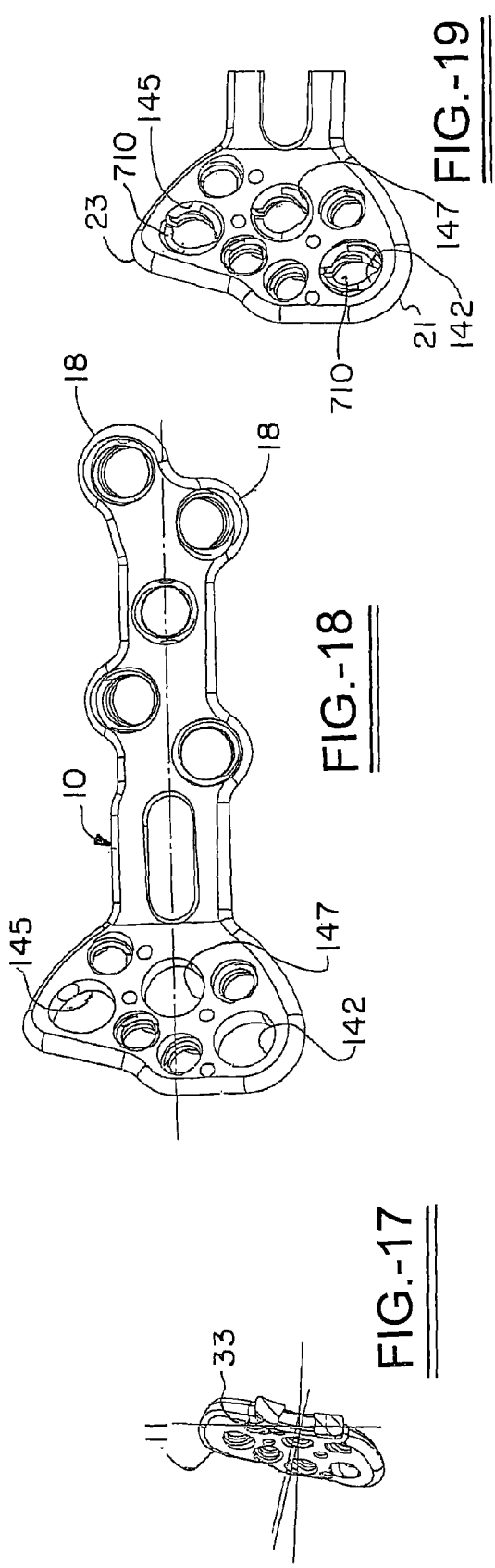

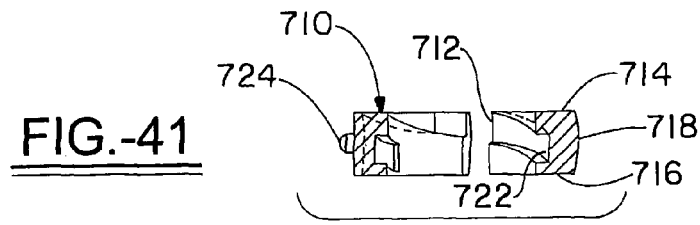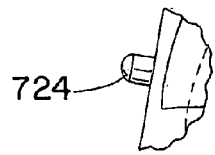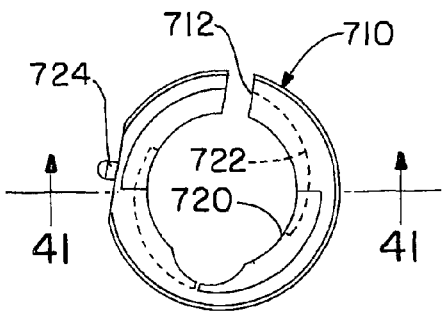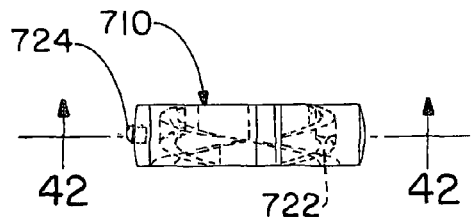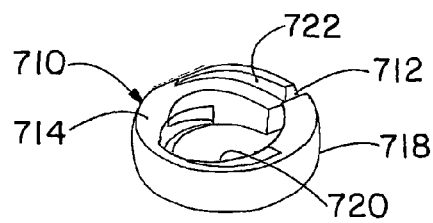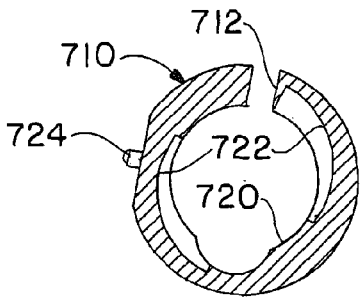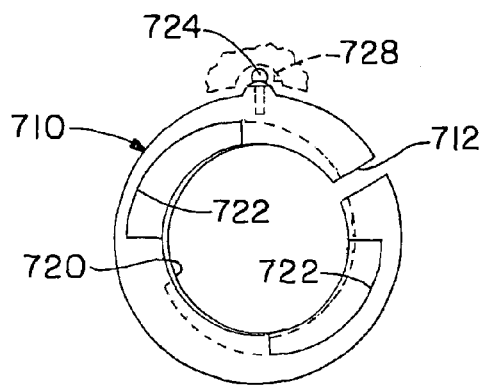

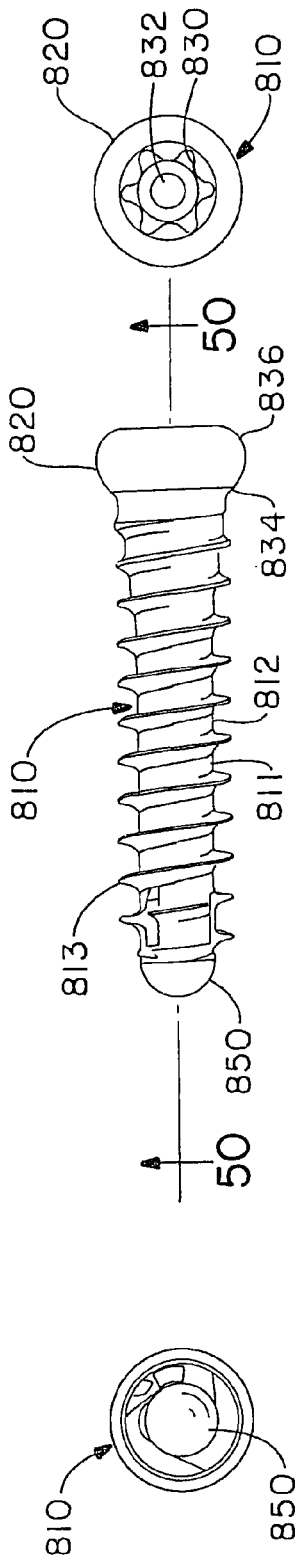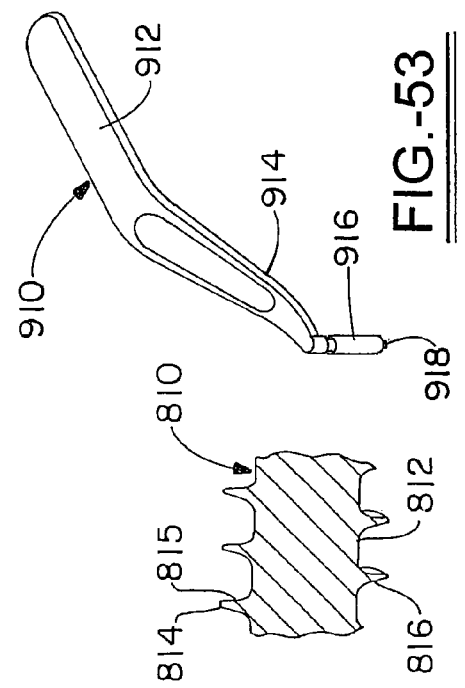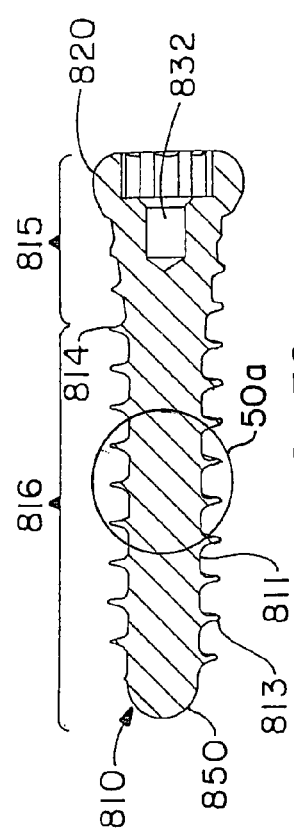

DISTAL RADIUS PLATE

This application is based on U.S. Provisional Application Ser. No. 60/779,865, filed on Mar. 7, 2006.

FIELD OF THE INVENTION

The present invention relates to an orthopedic plate for fixation of the radius bone, and further in particular to the distal terminus or head of a distal radial plate for internal fixation of a distal radial fracture.

BACKGROUND OF THE INVENTION

The wrist is the joint formed at the intersection of the radius, the ulna, the carpals and the metacarpals. The wrist is the most frequently injured area of the upper extremity with three fourths of wrist injuries involving a fracture of the distal radius, and/or of the radius. These injuries usually present in an emergency room setting, and often involve a fall on an outstretched hand. While the past conventional wisdom has included a belief that such injuries will tend to heal sufficiently on their own, there is often a loss of function and an early onset of arthritis that can be precipitated by the misdiagnosis and improper treatment of such injuries.

The treatments known for wrist trauma have included external stabilization and fixation such as by plaster casts, external fixators, and orthopedic plates. Casting alone, presents the possibility of misalignment of the fragments which can lead to severe loss of function and early onset of arthritis, if the fracture is not properly reduced, and/or if the fragments do not stay in a reduced state, in particular where the patient is not compliant. External fixators have been demonstrated to have an efficacy, but are cumbersome, cosmetically unappealing, and can lead to the possibility of infection at the attachment sites.

Accordingly, surgeons often consider methods of internal fixation, which typically include wire and/or screws, and plates. One issue with wires is that a construct is time-consuming to construct; and screws alone, often do not provide the stability required for fusion of the fragments. Plates have the benefit of providing a construct that is designed for ease of implantation, and at the same time have the disadvantage that there is a significant variety in the shape and size of individual bones. Further, in particular, the radius bone is relatively small so that individual variations are relatively more significant than in larger bones, such as the femur, the pelvis, and the humorous. Moreover, the flesh surrounding the radius on the underarm or volar (thumb) side is particularly dense with tendons, ligaments, nerves and blood vessels all of which are less forgiving of the intrusion of a metal construct than muscle or fatty tissue.

SUMMARY OF THE INVENTION

The plate in accordance with the present invention has a distal portion or head having a profile which flares from the sides of the plate to a leading edge that includes a central oblique linking area that helps to mark the placement of the plate relative to the radius. The head is shaped like a heart where the lobes have been asymmetrically truncated, like the palm of a hand, or like a modified kidney shape. The plate is designed to specifically accommodate the distal portion of the radial bone and further is provided in a right hand and left hand version, which are mirror images of each other. The thumb side of the head includes the most distally extending prominence, which also includes the highest elevation and is shaped to buttress the volar surface of the radial styloid. Extending from there in the direction of the pinky finger, the front edge of the head includes the central skewed or oblique linking area, which is a small oblique edge about two thirds of the way across the distal edge that leads from a first relatively transverse edge area into the second edge area of the distal edge that extends at a slight diagonal angle relative to the first edge area across the distal radius to a second prominence which sits under the ridge of the lunate fossa. Thus, the head profile curves upward, and outward from the proximal plate portion in a first rounded side into a first prominence which is the styloid prominence of the head to support the radial styloid on the volar side of the radius, and in a second rounded side on the other side to a second prominence which is the lunate prominence of the head to support the ridge of the lunate fossa on the volar side. The distal edge of the head forms two more or less, transverse segments between the first and second prominences with a skewed edge linking the first and second segments. The skewed area is intended to help locate the depression which is located toward the center of the radial bone, at the volar terminal of the ridge of the lunate fossa.

Further, the head has a complex topography in the Z direction which echoes a generalized shape for the distal volar surface of a radius. The lunate prominence of the head has a lower elevation in the Z direction than the elevation of the styloid prominence in the direction relative to the radius. The longitudinal axis at the center of the proximal portion of the bone defines the Y direction, and the X direction extends transverse in a direction in which the bone widens. Further, the plate includes an oblique depression, or cup, that extends from the rounded pinky side of the head and gradually morphs into the elevated styloid prominence in one diagonal direction and rises less gradually upward into the lunate prominence on the other side of the head. This distal cup undulates to define a superficial (i.e. relative to its surface) serpentine as it links into the proximal portion of the plate. The plate mimics the spiral of the radial bone as it extends proximally away from the distal portion. Thus, the proximal portion of the plate appears to twist or spiral along the longitudinal axis, and includes a tighter radial bend as it extends proximally since the bone becomes smaller and more circular in cross-section. Also in the longer embodiments, the plate curves along the longitudinal axis in the X direction toward the thumb side.

The plate is designed in general to accommodate the goal of being thick and/or rigid enough to provide optimal stabilization, and yet being as thin and therefore minimally invasive as possible given the general abundance of ligaments, blood vessels, and nerves in the indicated area. Strength is an issue for radial plates as the area of the distal radius is subject to surprisingly large forces that are generated by the tendons and ligaments of the hands in gripping objects. The plate is somewhat thicker in the neck area to provide for additional strength at the junction of the head and the proximal portion of the plate.

The head preferably includes holes or bores for pegs which extend into the distal portion of the radius to lock fragments into position. The plate is provided in a first and a second embodiment relative to the peg holes. In the first embodiment, the angles of the pegs are fixed, and more specifically, the angles of the axes of the pegs are fixed relative to an arbitrary origin located in the center of one of the screw holes in the proximal portion of the plate. The peg holes are threaded, and the peg angles are determined first by using a drill guide, which is in particular an individual drill guide that may be threaded into the threads of the peg hole (or may be tapered to allow for a friction fit, depending on the preference of the surgeon) and subsequently used to drill a guide hole into the bone. Generally, the pegs are threaded only at the top section although they may alternatively, or in combination, include threads along the body portion that is used to lock the bone into position relative to the plate. The threaded head of the pegs also preferably includes a taper in the minor diameter, which allows the peg to be locked into position in the plate as they are drawn into the closed position.

In the first embodiment, there are a plurality of fixed peg holes, including one in each of the styloid and lunate prominences (the first hole and the fourth hole), which splay outward and away from the plate such that they diverge away from one another to be capable of locking a styloid fragment and/or a fragment from the lunate fossa portion of the radial bone. A second hole, most distal hole is located generally under the skewed linking area of the head, which defines a peg axis that extends through the radius and distally toward the scaphoid or navicular bone and a third hole is distally aligned between the two holes of the prominences but is slightly backed off proximally from the second hole, with a peg axis that is more transverse than the peg axis of the second hole. The fourth peg hole is the hole of the lunate prominence which is slightly more proximal than the first hole which is located in the styloid prominence. A fifth hole is located in the first rounded side, which is on the styloid or thumbward side, toward the intersection between the proximal portion of the plate, and the plate head. The axis defined by this hole diverges outwardly toward the lateral portion of the radius (in a supine position). A sixth hole is located in a central portion of the head such as on a longitudinal axis of the plate, and a final seventh hole is located most proximally at the intersection of the head and the proximal portion of the plate, with the axis of the peg appearing to be more or less transverse relative to the plane defined by the opening of the peg hole.

In a second embodiment of the distal radial plate head of the present invention, one or more peg holes have a variable axis and one of more peg holes have an axis which is fixed. Preferably this embodiment includes a locking mechanism, which allows the pegs to be put in at a desired orientation and than locked. It is preferable that the head includes three variable locking pegs, and preferably, two of the three variable locking pegs are the pegs located in the styloid (hole 1) and lunate prominences (hole 4), and the third is located in the central portion of the head (i.e. hole number six above) and that the remainder of the holes are fixed.

The radial plate of the present invention further includes a proximal portion that extends longitudinally along the radial bone. The plate is intended to be placed along the volar, medial and/or lateral surface of the radial bone. The proximal portion has a curved surface which faces, or in some, but not necessarily all instances, touches the radial surface. More specifically, the curved surface is intended broadly to face the bone and to touch along its surface so as to support it on the radially facing surface of the plate (i.e. the surface facing the surface of the radial bone) so much as is allowed given the particular variations in individual bones. This proximal portion of the plate changes the radial as defined by a cross-section taken in the Z plane normal to the longitudinal axis of the plate curve as it advances proximally along the bone from a shallower to a sharper radius, and further spirals downward toward the side of the plate which includes the lunate prominence. The proximal portion has a plurality of screw holes, including one or more which are positioned along a central portion of the proximal portion of the plate and further includes two or more which are offset from the central portion of the plate. The screw holes are threaded so as to accept screws having threaded heads which will lock into position, or alternatively so that a screw with a rounded smooth head can be screwed into the bone and mesh with the internal threads of the screw holes.

In one embodiment, the proximal portion of the plate includes a proximal set of tabs or "ears" which are offset from the longitudinal axis of the plate, and further which allow the placement of screw holes that are offset from the longitudinal axis of the plate, as well as being offset longitudinally from each other. This allows the plate to be contoured about the circumference of the radial bone, and for the screws to be positioned at convergent angles to provide for better pullout values, i.e. such that it requires a greater force to pull the screws from the bone. This embodiment may also include an intermediate set of ears that similarly have a pair of offset intermediate threaded screw holes that are both longitudinally and laterally, or radially offset from the longitudinal axis of the plate, and which accept screws so as to have their axes at convergent angles. Again, the feature provides for better pullout values, and helps to avoid interference of the screws in the bone. The plate includes a central screw hole which is located between the proximal pair of ears, and the intermediate pair of ears. This screw hole is preferably positioned so that the axis forms a right angle relative to the longitudinal axis of the plate, and further relative to a lateral axis through the hole. Thus, a point in the center of the central screw hole can be used to define the origin of the plate, and the angles of the screw and pegs holes can be referenced with X, Y, and Z coordinates relative to this central hole. Further, the topography of the head can be defined using this coordinate system, which permits the manufacture of the plate using computer generated imaging.

Distal to the intermediate pair of ears, the plate includes a slot which is radiused at either end to accept a screw having a head of the same dimensions as the threaded screw holes. The slot is elongated along the longitudinal axis of the plate. This allows the plate to be loosely attached by inserting a screw through the slot, and prior to tightening the plate can be slid in the longitudinal direction to determine the optimal location of the plate on the radius. The slot also allows the radial bone to be viewed through the plate. This feature can be especially useful in the event that a more proximal portion of the bone includes a fracture.

BRIEF DESCRIPTION OF THE DRAWINGS

FIG. 12 is a view taken from the radial styloid side edge of the plate of FIG. 1;

FIG. 13 is a view taken from the proximal edge of the plate of FIG. 1;

FIG. 14 is a section of the plate taken along line 14-14 of FIG. 1;

FIG. 14A is a detail of the screw hole of FIG. 14;

FIG. 15 is a view from the side of the lunate prominence with the plate head in a lowered orientation and viewing the head in partial section to illustrate the detail of the threads of the peg holes;

FIG. 15A is a detail of the peg holes from FIG. 15;

FIG. 16 is a top view of the plate of FIG. 1 showing the lines at which the lateral sections of FIGS. 16A through 16G;

FIG. 16A is a section in the Y direction taken at line 16a of FIG. 16;

FIG. 16B is a section in the Y direction taken at line 16b of FIG. 16;

FIG. 16C is a section in the Y direction taken at line 16c of FIG. 16;

FIG. 16D is a section in the Y direction taken at line 16d of FIG. 16;

FIG. 16E is a section in the Y direction taken at line 16e of FIG. 16;

FIG. 16F is a section in the Y direction taken at line 16f of FIG. 16;

FIG. 16G is a section in the Y direction taken at line 16g of FIG. 16 are taken;

FIG. 17 is a cross section of the plate of FIG. 1 taken at line 17-17;

FIG. 18 is a top view of a second embodiment of the distal radius plate of the present invention;

FIG. 19 is a view of the head of the distal radius plate of FIG. 18 with the locking cam inserts in position in the variable locking peg holes;

FIG. 20 is a top view of the plate of FIG. 18 with locking pegs, fixed pegs, and screws in position in the peg and screw holes of the plate;

FIG. 40 is a top view of the locking cam insert which can be used with the plate system of the present invention having the variable locking aspect of the invention;

FIG. 40A is a detail of the stop pin from FIG. 40;

FIG. 41 is a cross section of the locking cam insert of FIG. 40 taken along line 40-40;

FIG. 42 is a cross section of the locking cam insert of FIG. 40 taken along line 42-42 in FIG. 41;

FIG. 43 is a side view of the locking cam insert of FIG. 40 showing the cam raceway in phantom;

FIG. 44 is a top view of the plate in accordance with the present invention with the locking cam insert in position, and showing the stop recess in the plate in phantom;

FIG. 49 is a side view of a non-locking screw that can be used as part of the plate system of the present invention;

FIG. 50 is a cross section of the non-locking screw of FIG. 49 taken along line 50-50 of FIG. 49;

FIG. 50A is a detail of the thread of FIG. 50;

FIG. 51 is an end view of the insertion tip of the screw of FIG. 49;

FIG. 52 is an end view of the torque receiving recess of the head of the screw of FIG. 49; and FIG. 53 is a top perspective view of a drill guide that can be used with the plate system of the present invention.

DETAILED DESCRIPTION OF THE DRAWINGS

Figure 1:
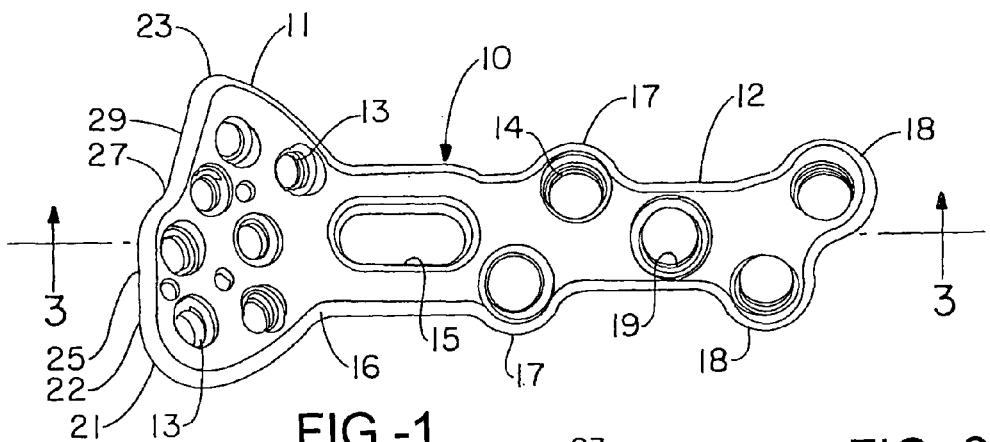
FIG. 1 is a top view of the distal radial plate and plate head in accordance with a first embodiment of the invention.
Figure 2:
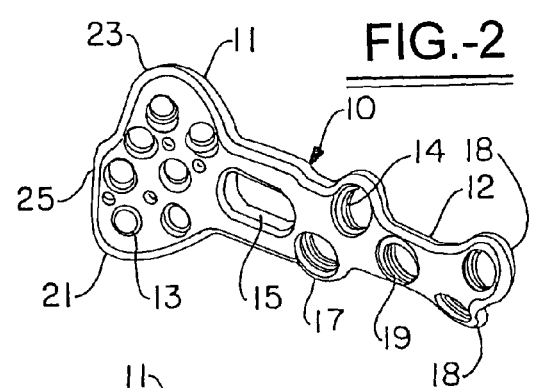
FIG. 2 is a perspective view of the plate of FIG. 1 viewed from the outer proximal surface looking toward the head with the styloid side of the plate downward.
Figure 3:
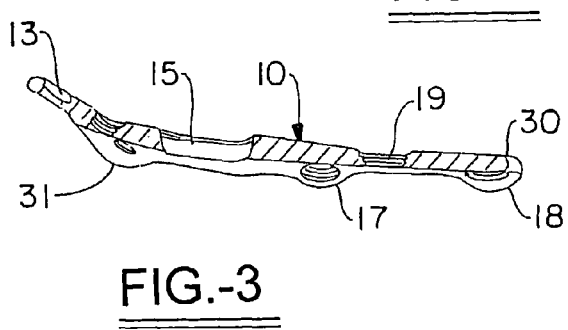
FIG. 3 is a cross section of the plate of FIG. 1 taken along line 3-3 in FIG. 1.
Figure 4:
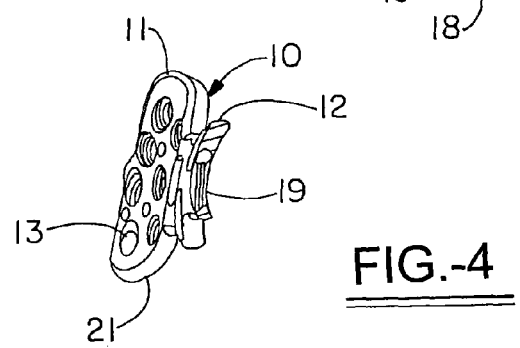
FIG. 4 is a cross section of the plate of FIG. 3 taken along line 4-4 in FIG. 3.
Figure 3A:
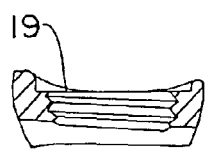
FIG. 3A is a detailed view of the central screw hole of FIG. 3.
Figure 5A:
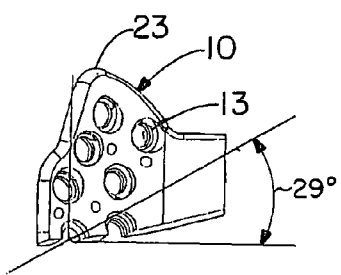
FIG. 5A is a detail of the head of the distal radial plate of FIG. 1 showing the angle of the axis of the screw for hole 1 in the XY plane.
Figure 5B:
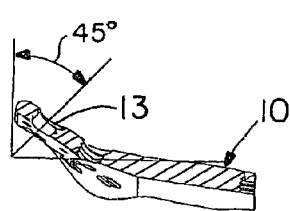
FIG. 5B is a detail of the head of the distal radial plate of FIG. 1 showing the angle of the axis of the screw for hole 1 in the XZ plane.
Figure 5C:
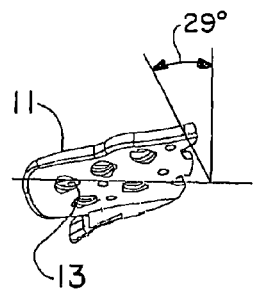
FIG. 5C is a detail of the head of the distal radial plate of FIG. 1 showing the angle of the axis of the screw for hole 1 in the YZ plane.
Figure 6A:
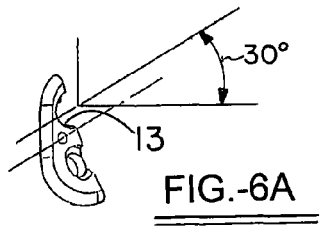
FIG. 6A is a detail of the head of the distal radial plate of FIG. 1 showing the angle of the axis of the screw for hole 2 and hole K2 in the XY plane.
Figure 6B:
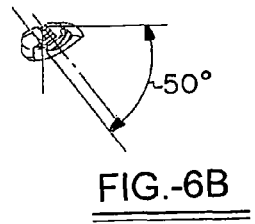
FIG. 6B is a detail of the head of the distal radial plate of FIG. 1 showing the angle of the axis of the screw for hole 2 and hole K2 in the XZ plane.
Figure 6C:
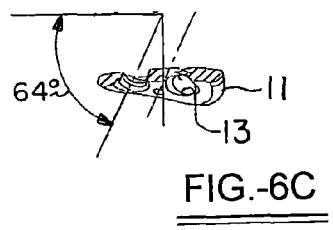
FIG. 6C is a detail of the head of the distal radial plate of FIG. 1 showing the angle of the axis of the screw for hole 2 and hole K2 in the YZ plane.
Figure 7A:
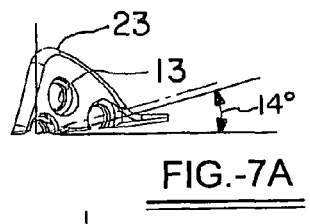
FIG. 7A is a detail of the head of the distal radial plate of FIG. 1 showing the angle of the axis of the screw for hole 3 and hole K3 in the XY plane.
Figure 7B:
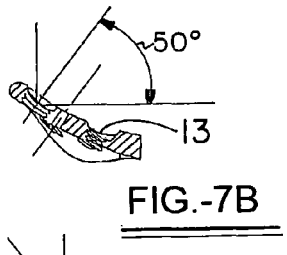
FIG. 7B is a detail of the head of the distal radial plate of FIG. 1 showing the angle of the axis of the screw for hole 3 and hole K3 in the XZ plane.
Figure 7C:
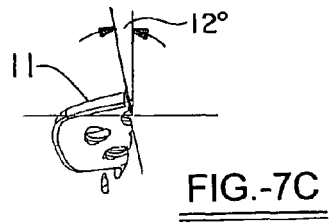
FIG. 7C is a detail of the head of the distal radial plate of FIG. 1 showing the angle of the axis of the screw for hole 3 and hole K3 in the YZ plane.
Figure 8A:
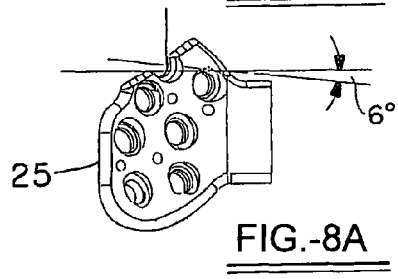
FIG. 8A is a detail of the head of the distal radial plate of FIG. 1 showing the angle of the axis of the screw for hole 4 in the XY plane.
Figure 8B:
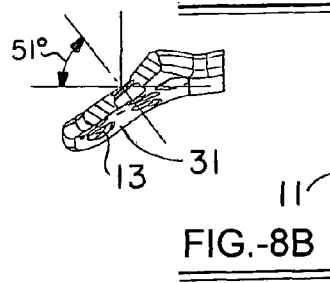
FIG. 8B is a detail of the head of the distal radial plate of FIG. 1 showing the angle of the axis of the screw for hole 4 in the XZ plane.
Figure 8C:
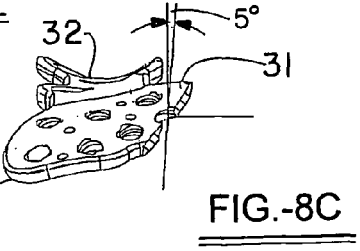
FIG. 8C is a detail of the head of the distal radial plate of FIG. 1 showing the angle of the axis of the screw for hole 4 in the YZ plane.
Figure 9A:
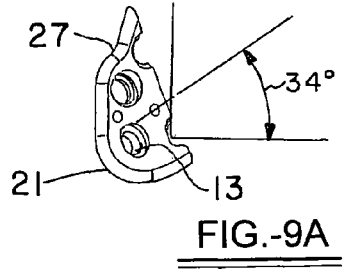
FIG. 9A is a detail of the head of the distal radial plate of FIG. 1 showing the angle of the axis of the screw for hole 5 and hole K5 in the XY plane.
Figure 9B:
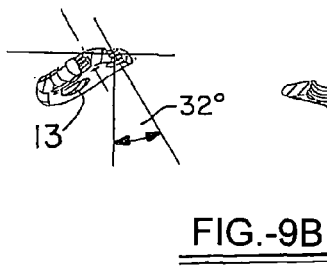
FIG. 9B is a detail of the head of the distal radial plate of FIG. 1 showing the angle of the axis of the screw for hole 5 and hole K5 in the XZ plane.
Figure 9C:
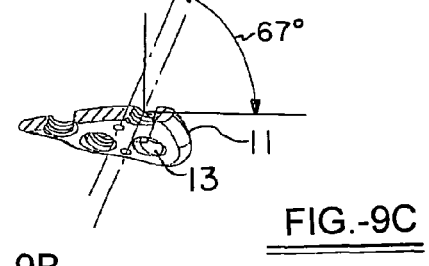
FIG. 9C is a detail of the head of the distal radial plate of FIG. 1 showing the angle of the axis of the screw for hole 5 and hole K5 in the YZ plane.
Figure 10A:
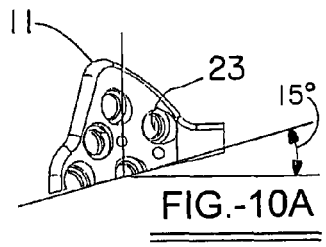
FIG. 10A is a detail of the head of the distal radial plate of FIG. 1 showing the angle of the axis of the screw for hole 6 in the XY plane.
Figure 10B:
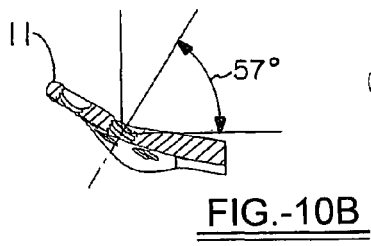
FIG. 10B is a detail of the head of the distal radial plate of FIG. 1 showing the angle of the axis of the screw for hole 6 in the XZ plane.
Figure 10C:
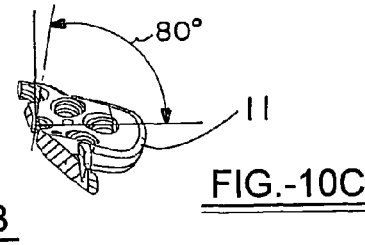
FIG. 10C is a detail of the head of the distal radial plate of FIG. 1 showing the angle of the axis of the screw for hole 6 in the YZ plane.
Figure 11A:
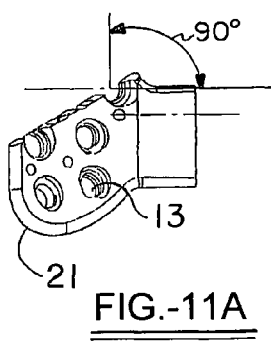
FIG. 11A is a detail of the head of the distal radial plate of FIG. 1 showing the angle of the axis of the screw for hole 7 and hole K7 in the XY plane.
Figure 11B:
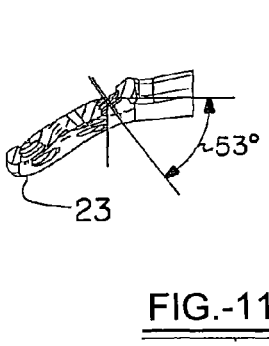
FIG. 11B is a detail of the head of the distal radial plate of FIG. 1 showing the angle of the axis of the screw for hole 7 and hole K7 in the XZ plane.
Figure 11C:
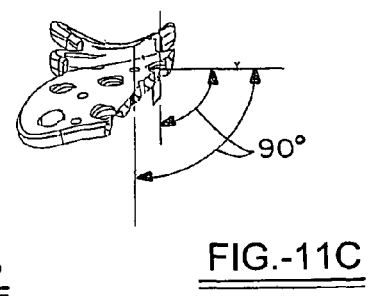
FIG. 11C is a detail of the head of the distal radial plate of FIG. 1 showing the angle of the axis of the screw for hole 7 and hole K7 in the YZ plane.
Figure 21:
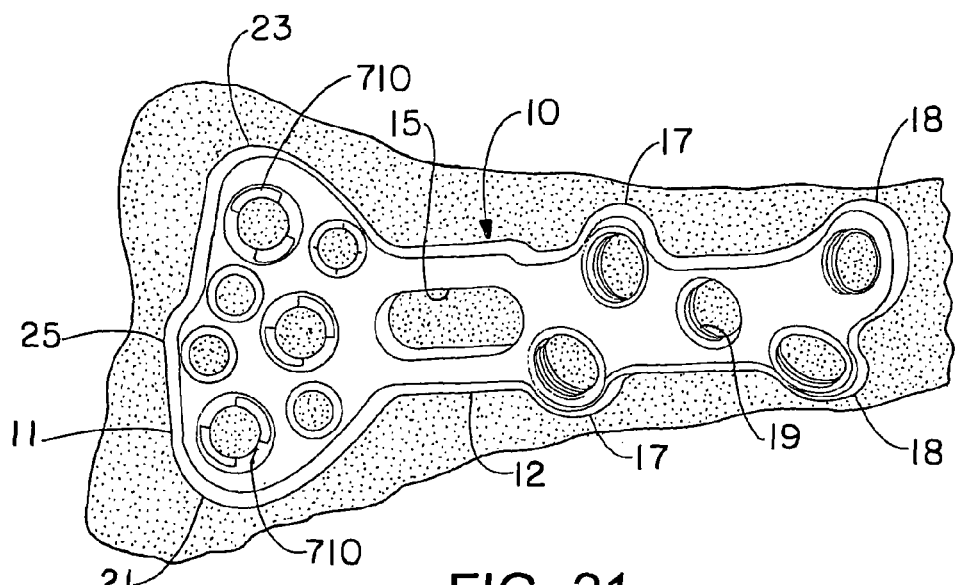
FIG. 21 is a top view of the plate in accordance with the second embodiment of the invention in position on a radial bone.

The present invention relates to an orthopedic plate that can be used to stabilize the fracture of a radial bone. A first embodiment of the plate is shown generally at 10 in FIG. 1 which includes a first, most distal portion or head 11 which has a profile from the top view similar to the palm of a hand, or which is shaped like a truncated heart, or a modified kidney shape. The head 11 slopes upward in a complex and organic topography away from the more elongated inversely curving proximal portion 12 of the plate. The head 11 includes a plurality of holes 13 for pegs, which holes can be internally threaded or not, or can also include means to provide for a variable locking axis. The proximal plate portion 12 also includes a plurality of holes 14 for screws, which similarly can include internal threads, or be smooth, or include means for a variable locking axis screw. The proximal portion of the plate also includes a slot 15 which is situated near the junction of the head 11 and the proximal portion of the plate, or the neck 16. The slot 15 can have a smooth internal edge, or can include a textured feature, such as grooves or tracks. The proximal portion also has two sets of tabs or ears, an intermediate pair 17 and a terminal pair 18 which each extend laterally from the longitudinal profile of the plate, and which provide for opposing screw holes that are each offset from the longitudinal axis of the plate and from each other along the longitudinal axis. The central point of a central screw hole 19 provides a point of reference or origin for mapping in three dimensions the topography or superficial locus of any point on the plate, which in turn enables the plate to be made having the complex curving fully contoured configuration that it does. The offset ears provide for convergence of the screws in the proximal or plate portion 12 of the distal radius plate while still avoiding screw interference, while providing for improved pullout strength as compared to a version where the proximal screws are located along a line, such as the longitudinal axis. The edge of the plate may be planar, and so may be surface features, such as an edge about a bore or "counterbore". However, the bone facing or contacting surface of the plate is designed to correspond to the surface of an idealized bone that represents a generalization of a collection of bones. In this sense, the plate has a lower surface which is substantially free from planes (again meaning that there are no planar surfaces of a size that would defeat the correspondence of the plate with the intended bone site.

The head portion 11 of the plate has a complex profile which is rounded on either side away from the neck area 16 to form a first prominence 21 and a second prominence 23. The first prominence 21 has a more gradual curve than the second prominence and is also the more distally extending of the two prominences. It is intended to support the radial styloid, and thus is termed the styloid prominence herein. The plate is provided in a left and a right version, which are mirror images of each other. The plate is generally intended to be implanted on the volar side of the radius (i.e. the top side when the arm is supine, and the palm is pointed upward). The styloid prominence 21 is thus on the lateral facing side of the plate, or the thumbward side. The second prominence 23 is designed to fit under the ridge of the lunate process, and is thus termed the "lunate" prominence herein. The distal edge 22 of the head 11 extends in a direction across the longitudinal axis of the proximal portion of the plate in three segments. A first portion 25 extends substantially transverse to the longitudinal axis of the plate to a point slightly more than, or about midway across the head of the plate. A second edge portion 27 links the first portion 25 and the third portion 29 and extends at an oblique angle proximally toward the third edge portion. The edge portion 27 or oblique link helps the surgeon to gauge the placement of the plate relative to the lunate ridge of the radial bone.

While the plate has tapering areas, the cross sectional dimension is generally sufficiently uniform that the contours of the top surface 30 generally mirror the contours of the bottom surface 31. In this context, "bottom" is used to mean the surface which faces, and which may, but does not necessarily have to touch the bone, and "top" means the outwardly facing surface. These surfaces undulate to mimic the shape or topography of the radial bone. More specifically, the bottom surface of the proximal portion of the plate includes a concavity or radius 32 along the longitudinal axis where the thumb side of the plate has a greater arc than the pinky side.

Figure 22:
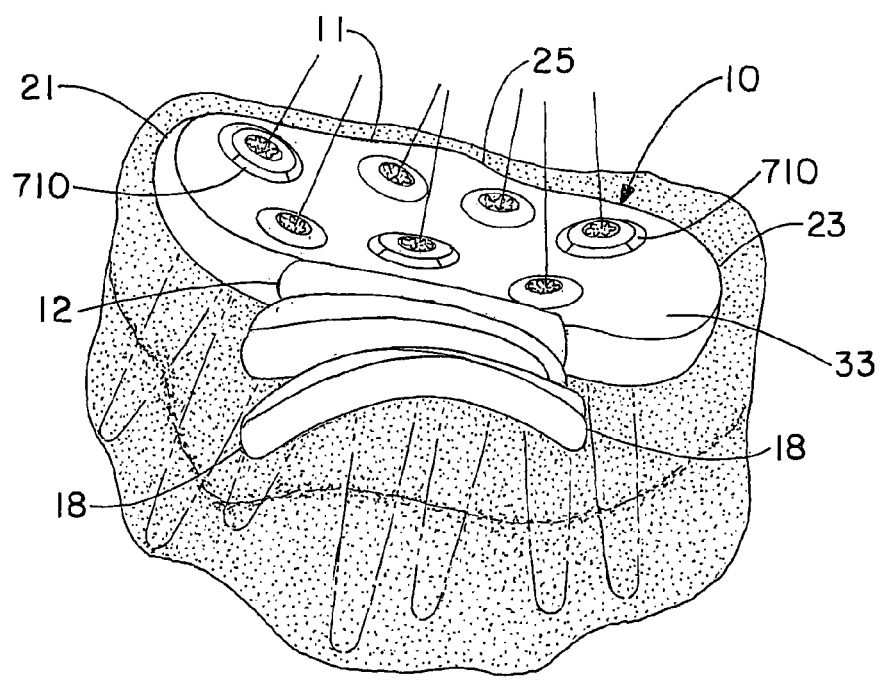
FIG. 22 is a view from the proximal portion of the radial bone showing the plate in accordance with the present invention in position on the volar side of the bone and illustrating the angles for the pegs.

As might best be viewed in FIG. 22, the pinky side of the plate, (i.e., in that view, the right side) forms a shallow serpentine on both the top and bottom surfaces which defines a gentle depression or cup 33 which is followed by a rise toward the lunate prominence 23 of the head. The cup extends and becomes shallower as the plate surface rises toward the styloid prominence, which has the highest elevation in the Z direction. Thus, particularly in the proximal portion, the plate appears to spiral along the longitudinal axis of the radial bone. FIG. 13 further illustrates this aspect of the plate in accordance with the invention where the X axis is taken through a central screw hole.

The topography of the plate is even more clearly shown in the sectional drawings FIGS. 16 through 16G which represent parallel slices taken in the Z planes at progressive locations along the longitudinal axis. It can be seen from these sections that the head portion 11 of the plate, as well as the proximal portion 12 of the plate is substantially non-planar, meaning that there is no significant portion of either the top surface or the bottom surface of either the head portion, or the proximal portion that defines a single plane. Instead, the head of the plate undulates from a central cup area that has a diagonal aspect from its lowest portion near the neck 16 of the plate on the pinky side of the head to the highest portion at the distal area on the styloid side of the plate. Consequently, the plate has a depression 33 in the top side of the head which extends diagonally in the direction from the styloid prominence 21 toward the necked area 16 under the lunate prominence 23. Thus, the top or exterior surface of the head 11 has a slightly concave area or cupped area 33 and other areas, such as the styloid prominence 21 and the lunate prominence 23 which are slightly convex on the top surface 30, or which rise. This transition can be said to cause the head to have top and bottom surfaces 30, 31 which undulate as they transition from the proximal portion of the plate 12 to the head portion 11. Further, the proximal portion of the plate 12 includes a bottom surface 31 which is radiused to fit the curve of the bone as it extends proximally from the wrist joint toward the elbow joint. This concave, or radiused area changes as it extends along the longitudinal axis of the plate. In particular, the plate transitions from an area that is flatter in the vicinity of the neck 16, and which increases in the amount of curve as can be seen by comparing FIG. 16D through 16G which illustrate the cross-section of the plate at progressive proximal locations along the longitudinal axis. The cross section of the head 11 is illustrated in FIGS. 16A through 16C which shows the plate at progressive distal locations along the longitudinal axis of the plate.

The plate head 11 is further provided with a plurality of holes 40 which receive pegs that are implanted into the distal portion of the radius, or into fragments of the bone. In particular, the distal radius plate head of the present invention is presented in two embodiments. In a first embodiment, all of the holes define a fixed axis for the pegs which they receive. The pegs holes 40 include internal threads 41 which mate with locking threads on the head of the pegs and which therefore lock the pegs in position in the plate. Of course, the plate could include peg holes which have no internal threads, or some combination of threaded and non-threaded holes. Alternatively, pegs can be used with a plate having threaded holes, where the pegs are not threaded at the top, but include a head that fits within the major diameter of the internal threads. Thus, the pegs may be locking pegs which have threads that mate with threads in the holes, or may be free from threads at the head. Further, the pegs may be threaded or non-threaded at the shaft portion. Thus, the use of the term "pegs" may encompass screws and vice versa.

The holes include a distal hole 42 in the styloid prominence 21, and a hole in the lunate prominence 45 and one or more (two in the case shown) holes 43, 44 in the head intermediate to the two side holes. One or more proximal set of holes is also advantageously provided. For example, a hole 46 may be provided under the styloid hole 42 and a hole 48 may be provided proximal to the hole 45 in the lunate prominence 23, and a hole 47 may be provided between the hole 46 and the hole 48. The angles of these holes determine the angles of the pegs that they receive. The angles are defined on a three coordinate matrix where 0,0,0 is the origin and is located at the center of a central screw hole in the plate. FIGS. 5a through 8c defines the angles for each of the three axes for the holes. Further, the plate is shown as including smaller diameter holes for K wires which help with the placement and angulation of the pegs. Thus, the holes K43-K48 have similar orientations to the holes 43-48 (where no K holes are illustrated for holes 42, 45 and 47). The angles are set to provide for the most common dislocation of fragments and to provide for the optimal fixation using the pegs.

The design contemplates a plurality of fixed peg holes, including one 42, 45 in each of the styloid (i.e. hole one) and lunate prominences (i.e. hole four), which splay outward and away from the plate such that they diverge away from one another to be capable of locking a styloid fragment and/or a fragment from the lunate fossa portion of the radial bone. A second distal-most hole 43 is located generally under the skewed linking area of the head, which defines a peg axis that extends through the radius and distally toward the scaphoid or navicular bone and a third hole 44 is distally aligned between the two holes of the prominences but is slightly backed off proximally from the second hole, with a peg axis that is more transverse than the peg axis of the second hole. The fourth peg hole 45 is the hole of the lunate prominence which is slightly more proximal than the first hole which is located in the styloid prominence. A fifth hole 46 is located in the first rounded side, which is on the styloid or thumbward side, toward the intersection between the proximal portion of the plate, and the plate head. The axis defined by this hole diverges outwardly toward the lateral portion of the radius (in a supine position). A sixth hole 47 is located in a central portion of the head such as on a longitudinal axis of the plate, and a final seventh hole 48 is located most proximally at the intersection of the head 11 and the proximal portion of the plate 12 at the neck 16 of the plate, with the axis of the peg appearing to be more or less transverse relative to the plane defined by the opening of the peg hole.

In a further embodiment of the invention, pegs are included which have a variable axis with a locking mechanism. It is particularly preferred that the plate include the fixed and variable axis type of pegs. FIGS. 18 through 22, and 25 through 27 illustrate this second embodiment of the invention. In particular, one or more of the peg holes in the head portion 111 of the plate 110 of the first embodiment may be replaced with variable locking pegs, or the pegs may be reoriented. The proximal portion 112 has the same features and is the same as previously described. In the embodiment shown, holes 42, 45, and 47 are each replaced with a variable locking mechanism 142, 145, and 147. The mechanism includes a camming mechanism on the head of the peg which mates with a cam locking insert that fits into and locks into a hole in the plate. The cam locking insert includes an anchor member that causes the cam locking insert to resist rotation as the camming members of the peg engage the cam raceway of the cam locking insert. This mechanism is described in greater detail hereinafter.

Figure 23:
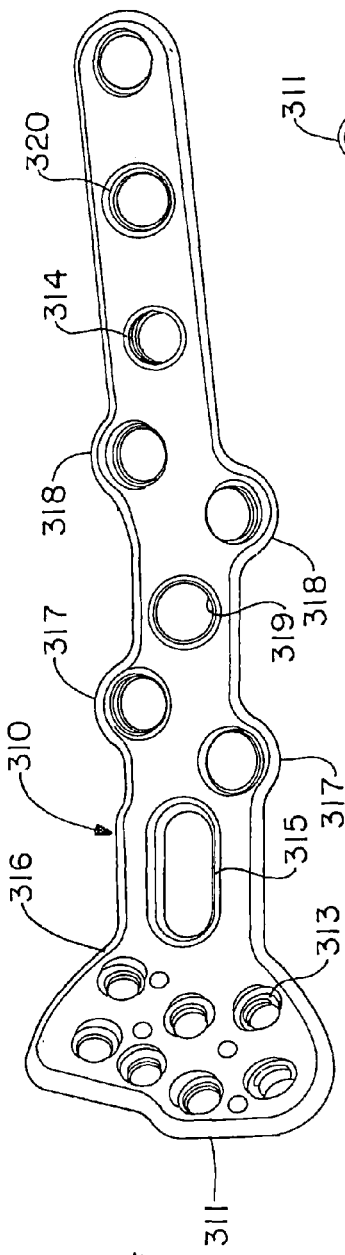
FIG. 23 is a top view of a third embodiment of the distal radial plate of the present invention with fixed angle pegs, and having an extended proximal portion.
Figure 24:
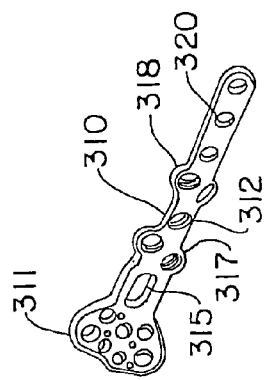
FIG. 24 is a side perspective view of the embodiment of FIG. 23.
Figure 25:
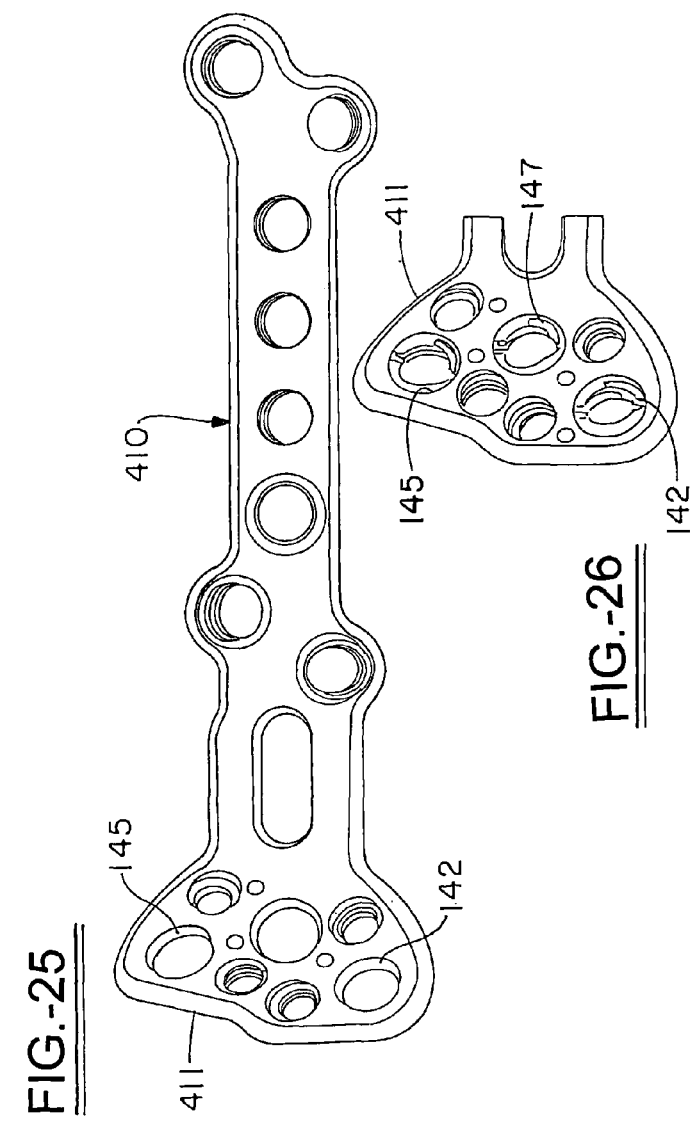
FIG. 25 is a top view of a fourth embodiment of the distal radial plate of the present invention with both fixed angle and variable angle locking pegs, and having an extended proximal portion.
Figure 26:
FIG. 26 is a detail of the head of the distal radial plate of FIG. 25 showing the locking cam inserts in position in the peg holes of the head.
Figure 27:
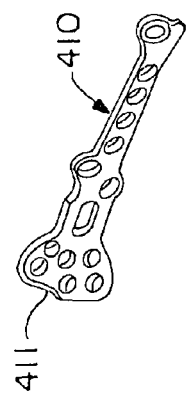
FIG. 27 is a side perspective view of the embodiment of FIG. 25.
Figure 28:
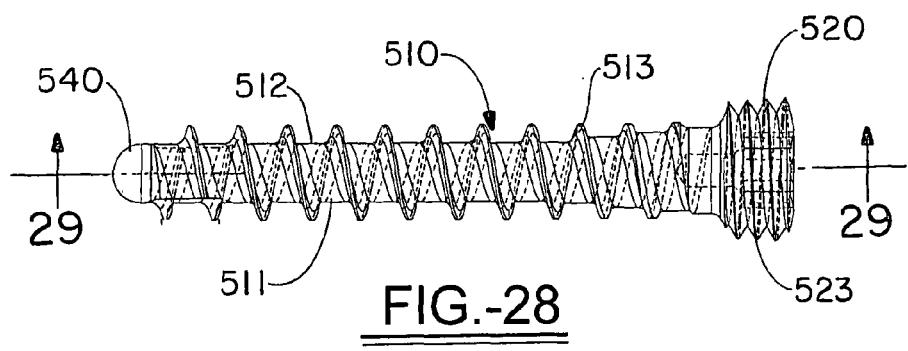
FIG. 28 is a side view of a locking screw that can be used as part of the plate system of the present invention.

As an additional aspect of the invention, a distal radius plate is provided which has an elongated proximal portion. This design is illustrated in FIGS. 23 through 27 and is shown with a distal head having only fixed angle pegs and having both fixed and variable angle pegs. In the embodiment shown in FIGS. 23 and 24, the plate 310 has a distal portion, or head 311 and a proximal portion 312. The head portion includes pegs holes 313 which can be internally threaded so as to define screw holes having fixed axes as is shown in FIGS. 23 and 24, or as is illustrated in FIGS. 25, 26 and 27, one or more of the fixed peg holes may be replaced with a variable axis mechanism, that advantageously also provides for locking of the angle of the axis.

The elongated version of the plate includes the features of the previously described version, with screw holes 314 in the proximal portion; an elongated slot 315 located along the central axis of the plate, adjacent the neck 316 which is the area that links the head 311, and the proximal portion 312. The elongated version of the plate further includes an intermediate tabbed area 317 having opposing offset ears that each receive a screw through an internally threaded screw hole, and a terminal tabbed area 318 that includes opposing offset ears that likewise each includes internally threaded screw holes. This version of the plate includes a central screw hole 319 that defines the origin for the coordinate system of the plate, and in addition, there are one or more additional longitudinally aligned screw holes 320. The elongated version of the plate has a proximal portion having a spiraling radiused portion similar to the shorter version except with a longer, and thus, more pronounced spiral, as can be seen in FIGS. 24 and 27. The fixed angle head 311 is the same as for the shorter version and the fixed angle head 11 of FIG. 1, and the head 411 shown in FIGS. 25-27 is the same as the head 111 shown in FIG. 18.

FIGS. 28 through 31 shows a locking screw which can be used in the head of the distal radius plate of the present invention. In particular, these screws 510 include a threaded shaft portion 511, and a threaded head 520. The shaft 511 has a minor diameter 512 about which the thread 513 spirals. The thread 513 includes a spiraling radial edge 514 best viewed in the thread detail FIG. 29a, which defines the major diameter. The thread further includes a front thrust face 515 which forms an angle of about 20°+/−5° to a plane transverse to the longitudinal axis of the screw. The trailing face 516 of the thread 513 forms an angle of about 5°+/−2° to the same plane.

Figure 29:
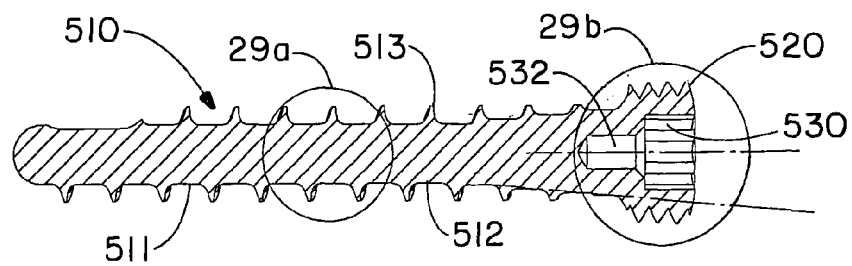
FIG. 29 is a cross section of the locking screw of FIG. 28 taken along line 29-29 of FIG. 28.
Figure 31A:
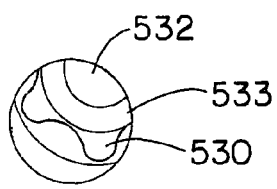
FIG. 31 is an end view of the torque receiving recess of the head of the screw of FIG. 28.
Figure 29A:
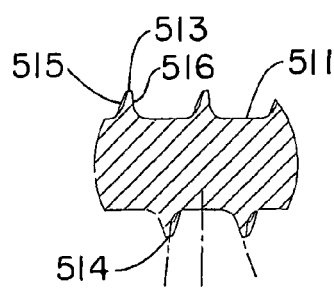
FIG. 29A is a detail of the screw thread of FIG. 29.
Figure 29B:
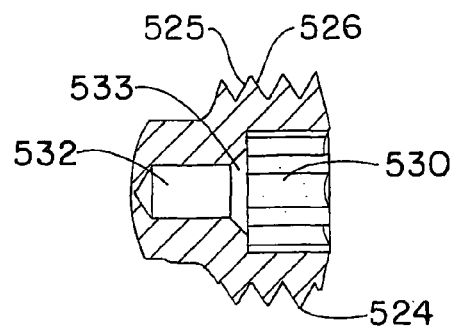
FIG. 29B is a detail of the screw head of FIG. 29.
Figure 32:
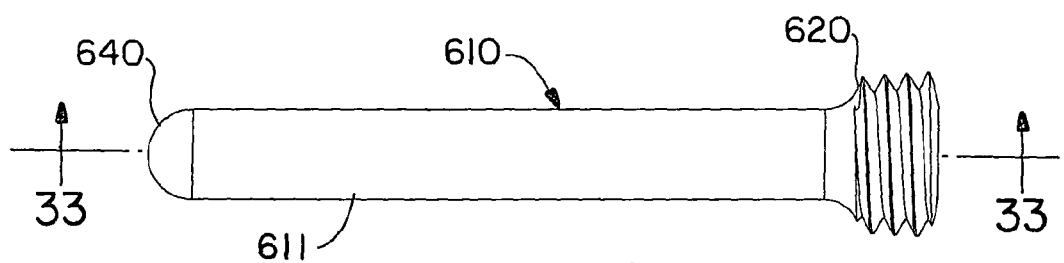
FIG. 32 is a side view of a smooth locking peg that can be used as part of the plate system of the present invention.

The head of the screw 520 includes external locking threads 523 as can be best viewed in the head detail in FIG. 29b. These threads also include a radial edge 524, a front thrust face 525, and a trailing face 526. The angle of the front thrust face 525 is the same as the angle of the trailing face relative to a plane which transverses the longitudinal axis of the screw, and is about 30°+/−5° for each angle. Thus, the locking thread 523 on the head 520 of the screw is a symmetrical v-shaped thread when viewed in profile in cross section. The head 520 tapers along the longitudinal axis, in both the major and the minor diameter, by a similar amount, as is shown in FIG. 29b. For the smaller screw, the taper is 7°, or 3.5° per side when measured in cross-section. The larger screw is 20° or 10° per side in section.

Figure 31:
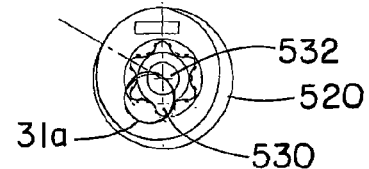

The head further includes a torque driving recess 530 which has a suitable shape to receive a torque driver. This is shown in FIGS. 29b and 31. The shape shown is a modified six lobed sinusoidal curve. The recess includes a central cylindrical bore 532 which receives the terminal post of a screwdriver to retain the screw on the driver. A transitional area 533 is angles to connect the recess 530 and the bore 532. The insertion tip 540 of the screw is blunt and preferably forms a portion of a sphere.

Figure 30:
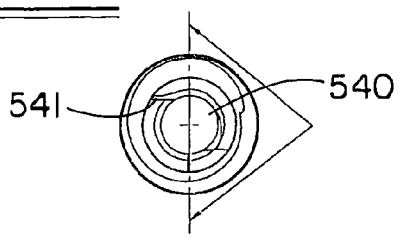
FIG. 30 is an end view of the insertion tip of the screw of FIG. 28.
Figure 33:
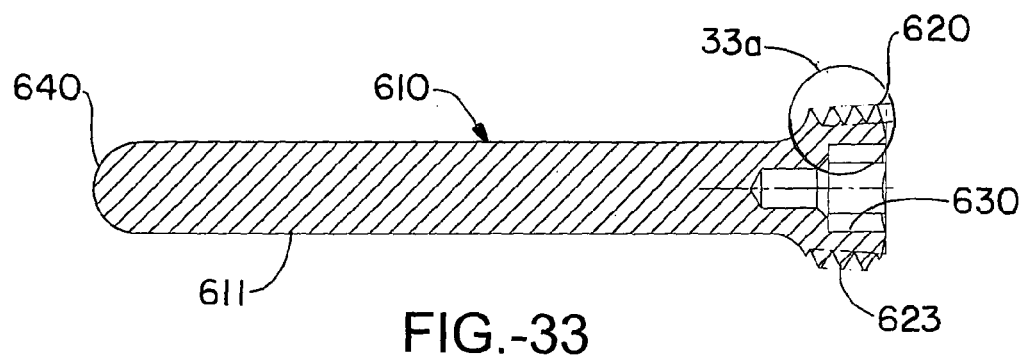
FIG. 33 is a cross section of the smooth locking peg of FIG. 32 taken along line 33-33 of FIG. 32.
Figure 34:
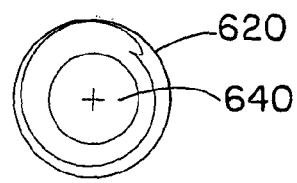
FIG. 34 is an end view of the insertion tip of the peg of FIG. 32.
Figure 35:
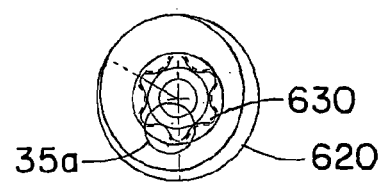
FIG. 35 is an end view of the torque receiving recess of the head of the peg of FIG. 32.
Figure 33A:
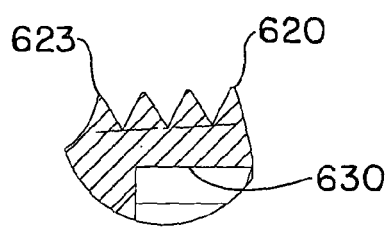
FIG. 33A is a detail of the locking thread of FIG. 32.
Figure 35A:
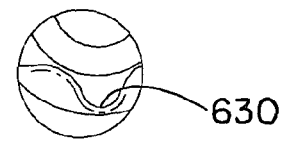
Figure 36:
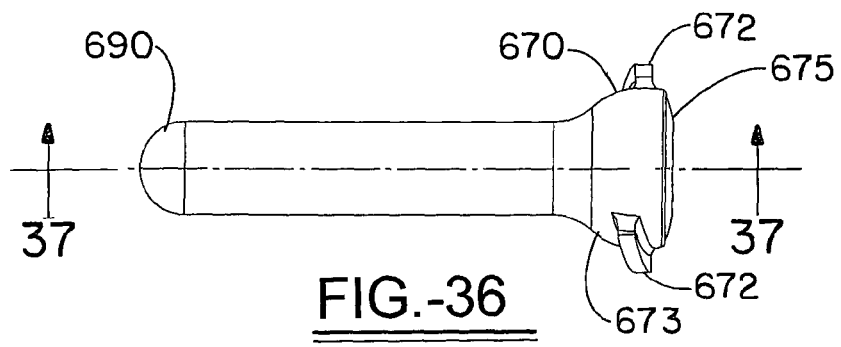
FIG. 36 is a side view of a smooth variable angle locking peg that can be used as part of the plate system of the present invention.

FIGS. 33 through 35 illustrate a distal locking peg 610 which is similar to the locking screws shown in FIGS. 29 through 31, except that the shaft of the peg 611 is not threaded. The head 620 however, includes locking threads 623 as previously described for the locking screw, and a torque driving recess 630 as previously described. The pegs further include a blunt or rounded insertion tip 640.

Figure 37:
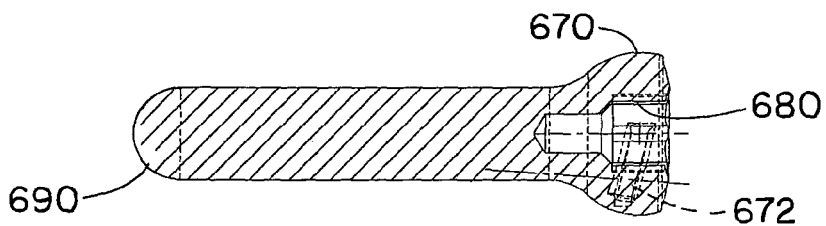
FIG. 37 is a cross section of the smooth variable locking peg of FIG. 36 taken along line 37 of FIG. 36.
Figure 38:
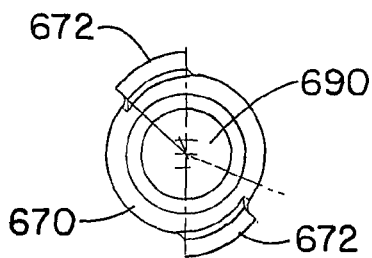
FIG. 38 is an end view of the insertion tip of the peg of FIG. 36.
Figure 37A:
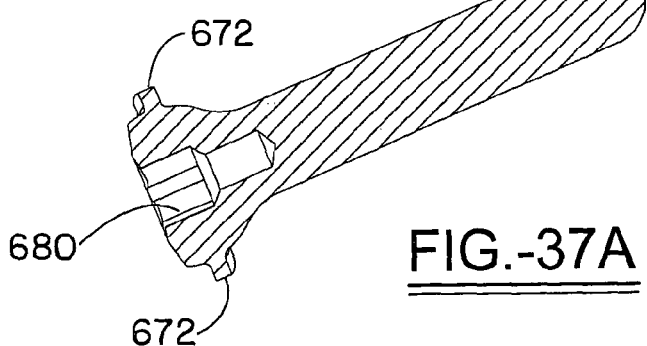
Figure 39:
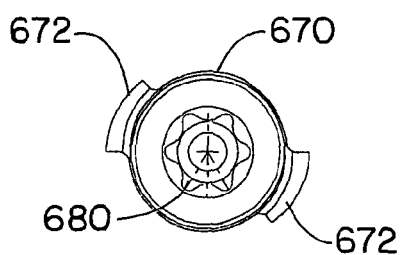
FIG. 39 is an end view of the torque receiving recess of the head of the peg of FIG. 36.
Figure 45:
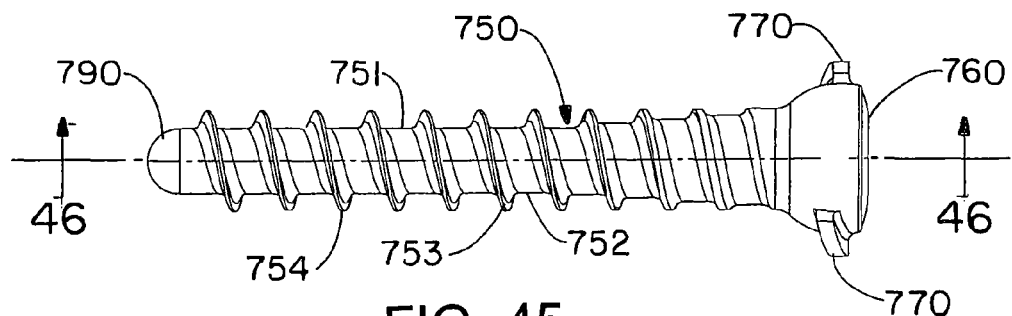
FIG. 45 is a side view of a threaded variable axis locking peg that can be used as part of the plate system of the present invention.
Figure 46:
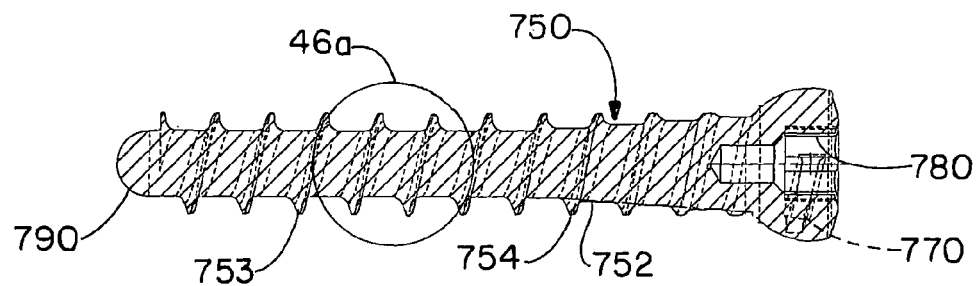
FIG. 46 is a cross section of the threaded variable peg of FIG. 45 taken along line 46-46 of FIG. 45.
Figure 47:
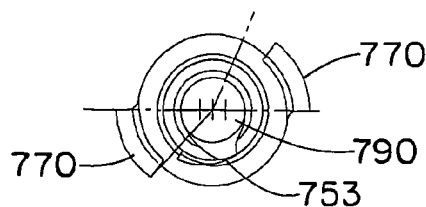
FIG. 47 is an end view of the insertion tip of the peg of FIG. 45.
Figure 48:
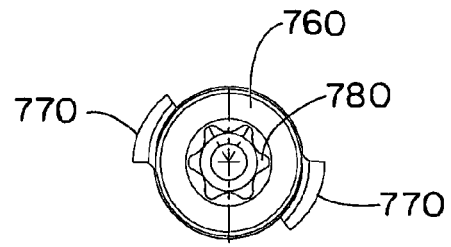
FIG. 48 is an end view of the torque receiving recess of the head of the peg of FIG. 45.
Figure 46A:
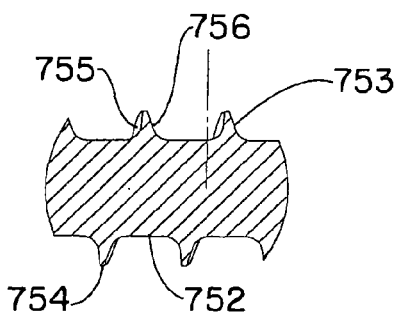
FIG. 46a is a detail of the thread of FIG. 45.
Figure 54:
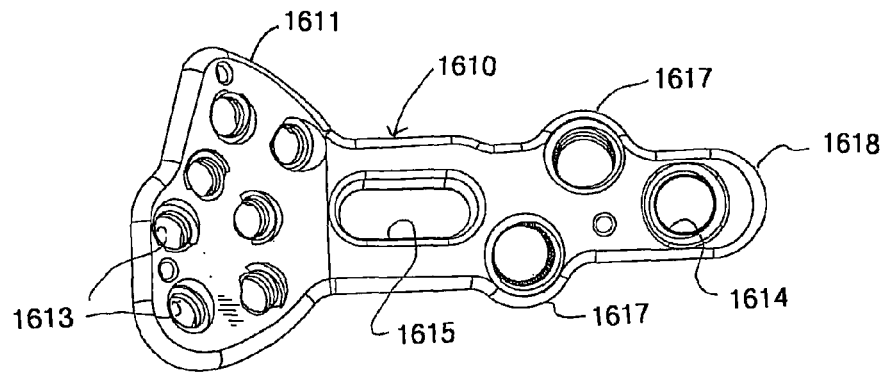
FIG. 54 is a top view of a short version of the orthopedic plate in accordance with the present invention.
Figure 55:
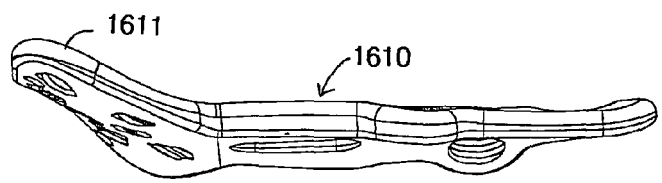
FIG. 55 is a first side view of the plate of FIG. 54.
Figure 56:
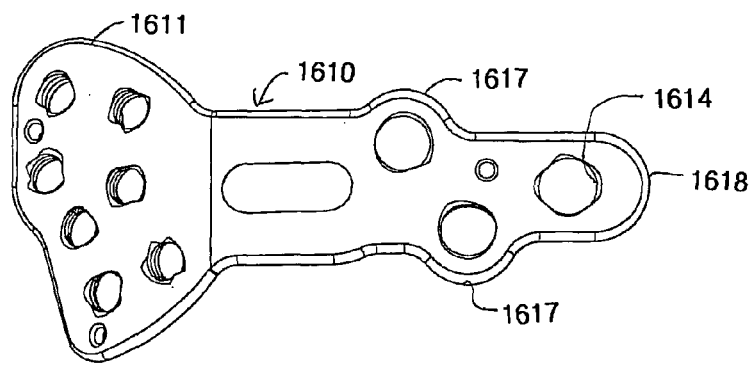
FIG. 56 is a bottom view of the plate of FIG. 54.
Figure 57:
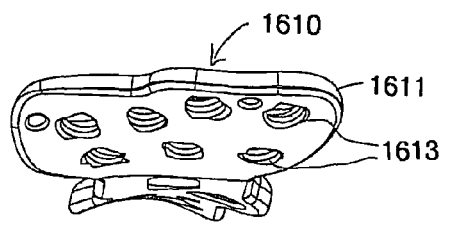
FIG. 57 is an edge view from the distal edge of the plate of FIG. 54.
Figure 58:
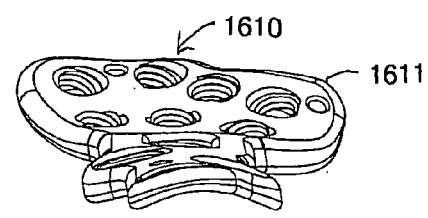
FIG. 58 is a edge view from the proximal edge of the plate of FIG. 54.
Figure 59:
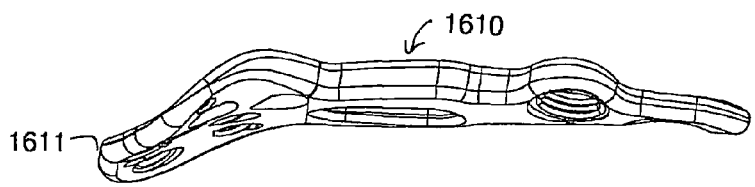
FIG. 59 is a second side view of the plate of FIG. 54.

FIGS. 36 through 39 shows a peg which can be used with the variable locking mechanism for the present invention. In particular, the peg 650 has a smooth shaft 651 with a rounded or blunt insertion tip 690. The shaft is connected by a neck area 652 to a locking head 670 which may include a torque driving recess 680 with a bore 682 both as previously described to provide for an interference fit with the post of a torque driver so that the peg is self-retained. The head 670 also includes a pair of wings 672 which act to engage the cam raceways in the cam insert 710 shown in FIGS. 40 through 43. While the camming mechanism is shown as including only two wings, it should be understood that the head could include more wings, and specifically three or four. The wings extend from about 40° to about 50° and spiral slightly from the base 673 of the head 670 upward toward the top surface 675. The base is slightly rounded. The wings have a quadrilateral cross section as can be seen in FIG. 37.

The camming insert is a generally circular or ring shaped insert 710 having an expansion gap 712 which is essentially a planar slice taken in the insert so as to create a gap. The insert 710 has a top surface 714 which is generally planar joined to a co-planar bottom surface 716 by an outwardly curving side surface 718. There is a concentric inwardly curving surface 720 which further includes the cam race 722, which in this case are two grooves that spiral a portion of the way down and around the inside surface. The grooves are open, and preferably only for a portion of the top 714 where the grooves are located. This open area of the race allows the cams to be introduced into the race. Subsequently, as the peg is turned in the camming insert, the cam engages the cam race and causes the insert to expand at the gap. This action causes the insert to lock in the recess 726 in the plate which receives the insert. Further, the insert 712 includes a stop 724. The stop is a projection that is received in a well 728 in the recess which retains the stop 724 and prohibits the cam insert from turning with the peg as it is turned relative to the plate.

FIGS. 45 through 48 show a variable axis locking screw 750 which is similar to the variable axis locking peg shown in FIGS. 36 through 39 and has a shaft 751 with a blunt or rounded insertion tip 790. The shaft 751 tapers throughout its length so that the screw 750 does not include a linking neck area as the peg does. The screw does include a locking head 760. The locking head includes a pair of cam wings 770 which are shaped as for the locking peg and which engage the race in the locking insert 710 in the same way as the cam wings of the variable locking peg. The shaft of the variable locking screw 750 is threaded with a thread 753 that is similar to the screw thread of the locking screw as shown and described for FIGS. 29 through 31 except that there is a taper to the minor diameter 752 of the shaft 751 toward the insertion tip 790 while the major diameter does not taper. The head 760 further includes a torque driving recess 780 with an optional bore 782 connected to the torque driving recess by a transitional area 781 which retains the screw 750 on the post of a screwdriver.

FIGS. 49 through 52 illustrate a proximal non-locking proximal screw 810 which is intended in particular for use in the proximal portion of the plate when it is desirable that the screw does not lock into the plate. The screw 810 has a shaft portion 811 having a thread 813 similar to the thread previously described for FIGS. 29 through 31. The thread 813 shown in FIGS. 49 through 52 has a taper in the minor diameter 812 over a portion 815 of the shaft 811, such as the first three turns of the thread. Thereafter, the terminal portion 816 of the shaft 811 has a constant minor diameter 812. The screw 810 has a blunt tip 850 and a rounded head 820 having a torque driving recess 830 optionally including a bore 832 to receive the post of a screwdriver to retain the screw on the screwdriver. The head has a spherically rounded lower portion 834 and a rounded upper portion 836 where the maximum outer diameter is smaller than the inner diameter of the threaded proximal screw holes.

FIG. 53 shows a drill guide for either the holes in the distal portion or for the holes in the proximal portion. The drill guide 910 includes an extending handle 912 with a tapering linking portion 914 and a post 916 which engages the hole in the plate. The post 916 has an internal hole for the drill bit and can have a smooth tapered surface at the terminal end 918 which engages the hole of the plate by friction, or the post end 918 can include threads to lock into the internal threads of the plate and to fix the angle for the fixed screws. FIGS. 29 through 34 show a further embodiment of the plate in accordance with the invention. This plate 1010 is comparable to the other embodiments in having a head 1011 joined to a proximal plate portion 1012. The head 1011 includes a plurality of peg holes 1013 as previously described and the proximal portion includes a plurality of screw holes 1014. This embodiment of the plate has only a single set of offset tabs 1017 which allows for convergent screws and the plate ends in a terminus 1018.

FIGS. 54 through 59 show a further embodiment of the plate in accordance with the invention. This plate 1610 is comparable to the other embodiments in having a head 1611 joined to a proximal plate portion 1612. The head 1611 includes a plurality of peg holes 1613 as previously described and the proximal portion includes a plurality of screw holes 1614. This embodiment of the plate has only a single set of offset tabs 1617 which allows for convergent screws and the plate ends in a terminus 1618.

While in accordance with the patent statutes the best mode and preferred embodiment have been set forth, the scope of the invention is not limited thereto, but rather by the scope of the attached claims.

What is claimed is:

1. A distal radius plate, comprising: a head portion and a proximal plate portion,
the head portion having a palm shaped profile having a top and bottom side and a complex topography that is substantially free from any planar areas, wherein the head portion has a first lateral side and a second lateral side and a first prominence on the first lateral side and a second prominence on the second lateral side, and the first prominence is more distal than the second prominence, wherein the head further has a first distal edge that extends from the first prominence toward the second prominence and a second distal edge that extends from the second prominence toward the first prominence and a linking area that extends between the first distal edge and the second distal edge;
wherein the head portion has a necked area at the juncture of the head portion and the proximal plate portion;
and wherein the head portion has a depression in the top side which extends diagonally in a direction from the first prominence toward the necked area under the second prominence.

2. The distal radius plate as set forth in claim 1, further including at least one peg and wherein the head further includes at least one through hole for the peg.

3. The distal radius plate as set forth in claim 2, wherein the head includes a plurality of through holes for the at least one peg.

4. The distal radius plate as set forth in claim 3, wherein the pegs holes each have an axis and at least two of the axes of the peg holes are not parallel.

5. The distal radius plate as set forth in claim 3, wherein the first prominence has a peg hole and the second prominence has a peg hole.

6. The distal radius plate as set forth in claim 4, wherein at least one of the peg holes includes a means for achieving a variable angle axis that can be locked into a position.

7. The distal radius plate as set forth in claim 1, wherein the bottom side of the proximal portion of the plate includes a concavely rounded portion.

8. The distal radius plate as set forth in claim 7, wherein the proximal portion of the plate has a length and the rounded portion of the proximal portion of the plate has a cross-sectional curve which changes along the length of the proximal portion of the plate.

9. The distal radius plate as set forth in claim 8, wherein the curve becomes tighter along the length of the plate as it progresses away from the juncture with the head.

10. The distal radius plate as set forth in claim 9, wherein the proximal portion of the plate forms a spiral along the length.

11. The distal radius plate as set forth in claim 10, wherein the proximal portion of the plate has a longitudinal axis and further includes at least one pair of a first tab extending from the first lateral side and a second tab extending from the second lateral side and each of the first tab and the second tab include a hole which is offset from the longitudinal axis of the proximal portion of the plate.

12. The distal radius plate as set forth in claim 11, wherein the proximal portion of the plate further includes a second pair of a first tab extending from the first lateral side and a second tab extending from the second lateral side and each of the first tab and the second tab of the second pair each include a hole which is offset from the longitudinal axis of the proximal portion of the plate.

13. The distal radius plate as set forth in claim 11, wherein the angles of the axes of the holes of the pair of tabs converge toward the bottom side of the plate.

14. The distal radius plate as set forth in claim 12, wherein the angles of the axes of each of the pairs of tabs converge toward the bottom side of the plate.

15. A distal radius plate, comprising: a head portion and a proximal plate portion, the head portion having a palm shaped profile having a complex topography substantially free from any planar areas, wherein the head portion has a top side and a bottom side, and the head portion further has a necked area at the juncture of the head portion and the proximal plate portion, wherein the head has a first lateral side and a second lateral side and a first prominence on the first lateral side and a second prominence on the second lateral side, the first prominence being more distal than the second prominence, wherein the head has a first distal edge that extends from the first prominence toward the second prominence and a second distal edge that extends from the second prominence toward the first prominence and a linking area that extends between the first distal edge and the second distal edge; and
wherein the head portion further has a depression in the top side which extends diagonally in a direction from the first prominence toward the necked area under the second prominence; and
wherein the plate has at least one fixed peg hole that is threaded and which defines a fixed angle for a peg which is received in the fixed peg hole and has at least one variable angle peg hole that has a variable angle locking mechanism that permits a variable angle peg to be received in the variable angle peg hole at a variable angle and subsequently to be locked into a desired position.

16. The distal radius plate as set forth in claim 15, wherein the bottom side of the proximal portion of the plate includes a concavely rounded portion.

17. The distal radius plate as set forth in claim 16, wherein the proximal portion of the plate has a length and the rounded portion of the proximal portion of the plate has a cross-sectional curve which changes along the length of the proximal portion of the plate.

18. The distal radius plate as set forth in claim 17, wherein the curve becomes tighter along the length of the plate as it progresses away from the juncture with the head.

19. The distal radius plate as set forth in claim 18, wherein the proximal portion of the plate forms a spiral along the length.

20. The distal radius plate as set forth in claim 19, wherein the proximal portion of the plate has a longitudinal axis and further includes at least one pair of a first tab extending from the first lateral side and a second tab extending from the second lateral side and each of the first tab and the second tab include a hole which is offset from the longitudinal axis of the proximal portion of the plate.

21. The distal radius plate as set forth in claim 20, wherein the proximal portion of the plate further includes a second pair of a first tab extending from the first lateral side and a second tab extending from the second lateral side and each of the first tab and the second tab of the second pair each include a hole which is offset from the longitudinal axis of the proximal portion of the plate.

22. The distal radius plate as set forth in claim 21, wherein the angles of the axes of the holes of the pair of tabs converge toward the bottom side of the plate.

23. The distal radius plate as set forth in claim 22, wherein the angles of the axes of each of the pairs of tabs converge toward the bottom side of the plate.

* * * * *